United States Patent [19]

Cope

[11] Patent Number: 4,960,407
[45] Date of Patent: Oct. 2, 1990

[54] DISPOSABLE EYE DROP DISPENSER INSTRUMENT FOR POST-SURGICAL AND GENERAL USE

[76] Inventor: Samuel M. Cope, 265 Western Promenade, Portland, Me. 04102

[21] Appl. No.: 357,485

[22] Filed: May 26, 1989

Related U.S. Application Data

[63] Continuation-in-part of Ser. No. 129,987, Dec. 8, 1987, Pat. No. 4,834,727.

[51] Int. Cl.⁵ .............................................. A61M 35/00
[52] U.S. Cl. .................................................... 604/300
[58] Field of Search .............................. 604/294–302

[56] References Cited

U.S. PATENT DOCUMENTS

| | | | |
|---|---|---|---|
| 2,722,216 | 11/1955 | Robbins | 128/233 |
| 2,898,911 | 8/1959 | Taylor | 128/249 |
| 3,058,466 | 10/1962 | Routsong | 128/233 |
| 3,314,426 | 4/1967 | Carroll | 128/173 |
| 3,409,009 | 11/1968 | Vasse | 604/298 |
| 3,598,121 | 8/1971 | Lelicoff | 128/233 |
| 3,872,866 | 3/1975 | Lelicoff | 128/233 |
| 4,002,168 | 1/1977 | Petterson | 128/233 |
| 4,085,750 | 4/1978 | Bosshold | 128/233 |
| 4,257,417 | 3/1981 | Gibilisco | 128/233 |
| 4,531,944 | 7/1985 | Bechtle | 604/302 |
| 4,543,096 | 9/1985 | Keene | 604/300 |
| 4,605,398 | 8/1986 | Herrick | 604/300 |
| 4,685,906 | 8/1987 | Murphy | 604/300 |
| 4,701,167 | 10/1987 | Chekan | 604/301 |
| 4,733,802 | 3/1988 | Sheldon | 604/302 |
| 4,834,728 | 5/1989 | McKenna | 604/301 |

FOREIGN PATENT DOCUMENTS

| | | |
|---|---|---|
| 594860 | 10/1932 | Fed. Rep. of Germany . |
| 722852 | 3/1932 | France . |
| 1025852 | 4/1953 | France . |
| 2142829 | 1/1985 | United Kingdom . |

Primary Examiner—Stephen C. Pellegrino
Assistant Examiner—Denise W. DeFranco
Attorney, Agent, or Firm—Fish & Richardson

[57] ABSTRACT

An instrument for delivery of liquid eye drop solution into the eye of a patient for post-surgical and general treatment includes a squeeze-type dispenser bottle and a device for positioning the bottle for dispensing solution. The bottle has a body defining a volume for eye drop solution, the body having a neck and shoulder region and a base, and a nozzle disposed above the neck and shoulder region. The nozzle defines an orifice for delivery of solution from the volume. The device positions the nozzle relative to an eye of a patient to be treated, and includes a generally oval ring contoured to fit within the orbital or periorbital area of a patient's body and at least one post extending from the oval ring generally perpendicular to a plane of the oval ring, the post attached at the neck and shoulder region of the bottle.

9 Claims, 13 Drawing Sheets

DISPOSABLE EYE DROP DISPENSER INSTRUMENT FOR POST-SURGICAL AND GENERAL USE

This application is a continuation-in-part of my application Ser. No. 129,987, filed Dec. 8, 1987, now U.S. Pat. No. 4,834,727, issued May 30, 1989.

This invention relates to instruments for holding plastic squeeze bottles to assist in the dispensing of medications and cleansing solutions by the drop or spray method onto the human eye.

BACKGROUND OF THE INVENTION

A variety of devices for accomplishing this purpose have been previously proposed. An example includes U.S. Pat. No. 2,898,911 which discloses a resilient eye cup capable of being snapped onto the shoulder of an eye drop bottle. U.S. Pat. No. 3,058,466 is directed to a bridge-like member arranged to hold a bottle, positioning being accomplished by placing the feet of the bridge above and below the eye. Still another prior art proposal appears in U.S. Pat. No. 3,872,866 which teaches threading a positioning device to the threads of a bottle neck. U.S. Pat. No. 4,085,750 shows resilient arms extending from a collar fitting the bottle neck, the idea being that the arms are engaged with the closed eyelid and allowed to spread to hold the lid open. French patent No. 1,025,304 (published 14 Apr. 1953) also discloses the use of arms but with the additional feature of rupturing the drop container when the arms are squeezed to release a fluid. It is clear that any device of this kind employing individual arms is dangerous when in use, having the potential for injuring the patient's eye.

It is the object of the present invention to provide a safe instrument which is easily and quickly attached, either removably or permanently, to a plastic eye dropper bottle to increase accuracy in dispensing ophthalmic solutions in post-surgical and general use and which may either be removed for reuse on another bottle or thrown away with the bottle when empty.

SUMMARY OF THE INVENTION

According to the invention, an instrument for delivery of drops of liquid eye drop solution into the eye of a patient for post-surgical and general treatment comprises a squeeze-type dispenser bottle comprising a body defining a volume for eye drop solution, the body having a neck and shoulder region and a base, and having a nozzle disposed above the neck and shoulder region and defining an orifice for delivery of solution from the volume, and a device for positioning the nozzle relative to an eye of a patient to be treated, the device comprising a generally oval ring contoured to fit the periorbital and intraorbital area of a patient's eye, at least one post extending from the oval ring generally perpendicular to a plane of the oval ring, and means for attachment of the post at the neck and shoulder region of the bottle.

In the preferred embodiments, the post comprises a main post section having a first end joined to the oval ring and a second end, and further comprises a stub post element disposed at the second end and extending generally perpendicular to the axis of the main post section, the bottle, in the neck and shoulder region, defining an orifice, the stub post being sized and adapted for fixed engagement within the orifice for attachment of the device upon the bottle, preferably the means for attachment is adapted for selective disposal of the oval ring in a first (use) position, with the ring centered about and spaced from the nozzle, and a second (store and carry) position with the oval ring disposed more adjacent the body of the bottle, more preferably the stub post is adapted for rotation in the orifice, and the oval ring in the second position is disposed adjacent the bottle base.

In another preferred embodiment, the post comprises a main post section having a first end joined to the oval ring and a second end, and further comprises a stub post element disposed at the second end and extending generally perpendicular to the axis of the main section of the post, the stub post forming an integral component of the bottle, preferably the means for attachment is adapted for selective disposal of the oval ring in a first (use) position, with the ring centered about and spaced from the nozzle, and a second (store and carry) position with the oval ring disposed more adjacent the body of the bottle.

In both of the above-described embodiments, the main post section may comprise a post element and a tube element, the post element being sized for frictional sliding engagement within the tube element; and the main post section may comprise a hinge element.

In another preferred embodiment, the device further comprises an apron sized and constructed for fixed engagement about the neck and shoulder region of the bottle, preferably the post comprises a main post section having a first end joined to the oval ring and a second end, and further comprises a stub post element disposed at the second end and extending generally perpendicular to the axis of the main post section, more preferably the stub is an integral element of the apron, still more preferably the device comprises at least two posts, the stub arm of each post defining an orifice, and the apron further comprises two projecting key elements sized and constructed for engagement within the stub post orifices, and the apron may further comprise a sleeve sized and constructed for rotational engagement about the stub arm.

According to another aspect of the invention, a device for use in association with a squeeze-type dispenser bottle for delivery of liquid eye drop solution into the eye of a patient for post-surgical and general treatment comprises a generally oval ring contoured to fit the periorbital area of a patient's body, at least one post extending from the oval ring generally perpendicular to a plane of the oval ring, the post having a first end joined to the oval ring and a second end, and means for attachment of the post to the eye dropper bottle, the means for attachment comprising a stub post at the second end of the post, the stub post disposed generally perpendicular to the axis of the post and joined to the dispenser bottle.

Other features and benefits of this invention include the following:

(a) Permits ease and safety in use of a squeeze bottle in the orbital area, by having surgically involved areas of the eye undisturbed;

(b) Directs nozzle tip of bottle to proper height and position over the eye to prevent accidental contact with eye;

(c) Prevents nozzle tip from contacting sources of contamination;

(d) Avoids waste of solution by directing deposit of solution to correct spot;

(e) When used for direct application within orbital area to the eyelids, retracts lower lid and could minimize blinking reflexes;

(f) Provides stability by assisting the elderly or incapacitated in effective application of solution;

(g) Psychologically assists patient and gives each individual a sense of security and independence;

(h) Application of drops does not require light, all procedures can be accomplished by touch;

(i) Could be used by young individuals;

(j) To avoid possible contamination after use by reuse on other bottles, the positioning device may be fixedly attached to the bottle, or a part of the device may be fixedly attached to the bottle for disposal therewith when empty, or the bottle may be altered at the shoulder area to permit individualized devices specifically adapted for use. A bottle ma be formed with the device integrally formed therewith as a step of manufacture.

Other objects, features and advantages of this invention will become apparent by referring to the following detailed description of presently preferred embodiments of the same taken in conjunction with the accompanying drawings.

BRIEF DESCRIPTION OF THE DRAWINGS

In the drawings,

FIG. 15 is a front view of the base rim portion of another embodiment of the device invention, while FIGS. 15A and 15B are similar views of alternate embodiments of the attachment portion of the device both suitable for use with the base rim portion of FIG. 15;

DESCRIPTION OF PREFERRED EMBODIMENTS

Reusable Version

Figure 1:
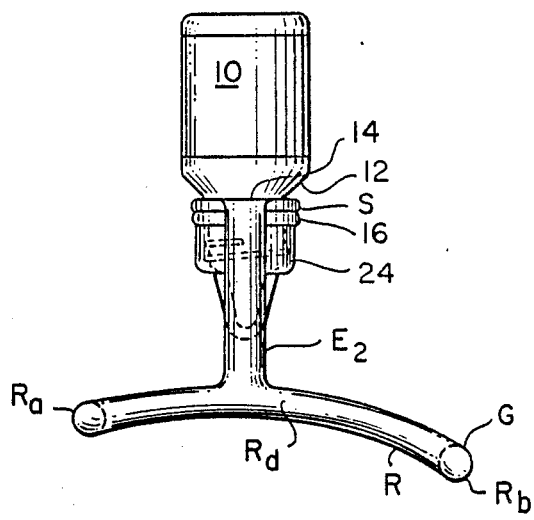
FIG. 1 is a front view of one preferred embodiment of the invention.

Plastic dispenser bottles for ophthalmic solutions are made in assorted sizes. Some have regular size spiral threads 18 and nozzle 20, while others have a long body, wider spirals yet usually the same size nozzle. The latter type bottle is at least ¼ inch longer from the base of the neck 16 to the nozzle tip 20.

The embodiments described below fit securely that part of the neck 14 of the bottle 10 which is located between the shoulder 12 and the base of the neck 16.

The remaining bottle parts are referred to as nozzle aperture 22 and cap 24.

Figure 2:
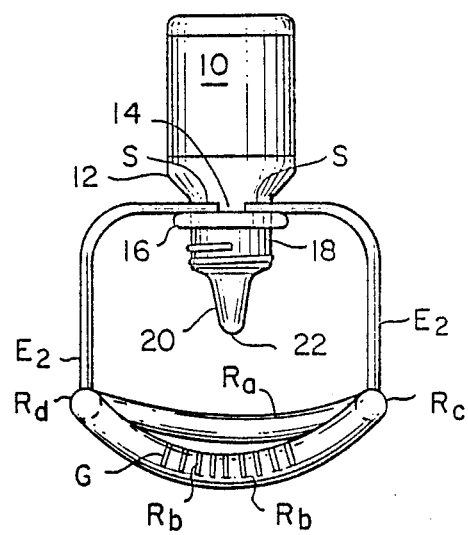
FIG. 2 is an end view of the same.

The embodiment of the invention shown in FIGS. 1 and 2 is a split ring attachment. Rim R is contoured to fit the periorbital area, with the rim at $R_c$ and $R_d$ concave at the bottom. Two posts $E_2$, one attached to the upper part of rim at $R_c$, and the other to the lower part of rim at $R_d$, are positioned slightly toward the medial aspect of the rim $R_a$. Posts $E_2$ are concave at the inner midsurface and converge towards the center at the top ends. Rather than straight converging posts, concave posts are used to retain flexibility and to allow for maximum available space in which to remove and replace the bottle cap 24. The top ends of posts $E_2$ support a rigid split ring S.

FIG. 1 is a front view with post $E_2$ on lower rim at $R_d$. The split ring S engages the neck of bottle 14 above the base of neck 16 and below the shoulder 12 of bottle.

FIG. 2 shows a correctly positioned dispenser bottle. To place the bottle into position, the operator grasps the upper part of both posts $E_2$ and pulls firmly in opposite directions to enlarge the area within the split ring S. The inverted bottle is inserted such that neck 14 is firmly grasped by split ring S. Posts $E_2$ have sufficient flexibility and tension to permit the split ring S to grip bottle neck 14 tightly.

The bottle 10 with nozzle tip 20 is now in the proper and safe position, high enough above the rim surface to avoid contact with any part of the eye.

Figure 3:
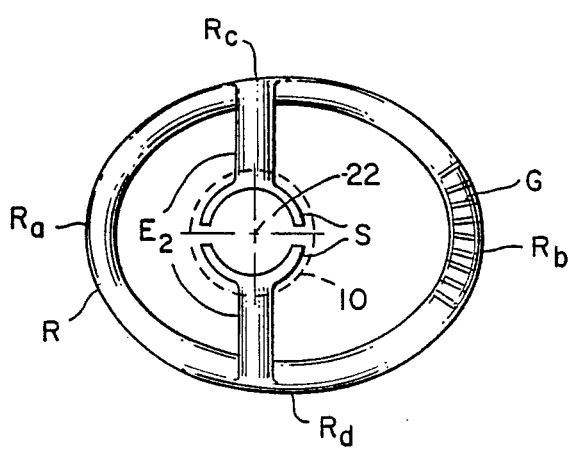
FIG. 3 is a plan view thereof.

FIG. 3 is a top plan view of the split ring embodiment with parts relatively positioned. The bottle 10, nozzle aperture 22 and cross grooves G are shown. Grooves G, which act as indicia to indicate placement direction to the user, should face outward. The assembled unit is rotated 180° to properly position for use on the opposite side of the patient's face.

Figure 4:
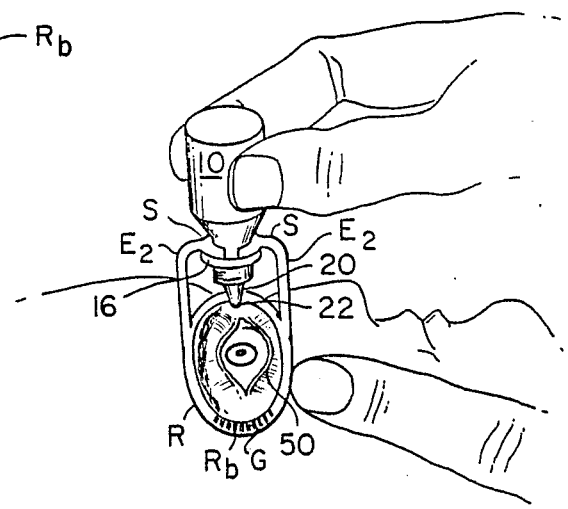
FIG. 4 is a perspective view showing this embodiment in use.

FIG. 4 is a perspective view (not to scale) of the same embodiment correctly positioned for use. In use, cap 24 is removed. For the right eye, with the patient's head tilted back as far as possible or with the patient in a prone position, the body of bottle 10 is held with thumb and forefinger of right hand and with cross grooves G toward the outer side of face, the instrument is brought toward the eye. Using the other hand, pressure is gently applied with the index finger or two fingers onto the soft tissues above the lower bony ridge, pulling the finger(s) and tissues down below the edge of the hard ridge, forming a cul-de-sac 50 and maintaining this position.

Rim R is positioned with three areas of contact: (1) lower part of rim $R_c$ placed at tip of finger nail(s), onto the soft tissues near the infra-orbital ridge; (2) upper part of rim $R_d$ at supra-orbital ridge; and (3) medial part of rim $R_a$ touching the side of the bridge of the nose. Keeping the upper lid open, and avoiding blinking if possible, the bottle 10 is squeezed with thumb and forefinger to deposit one or more drops onto the eye.

The instrument is then rotated a half turn using the same procedure to service the other eye. The cap 24 may be replaced and the bottle stored in an upright position with the instrument attached. Individuals with blinking reflexes may find it very helpful to insert drops by use of this technique.

Figure 5:
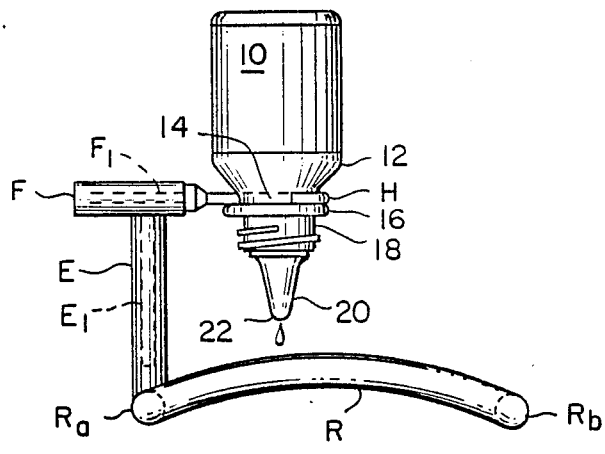
FIG. 5 is a front view of a second embodiment of the invention.
Figure 6:
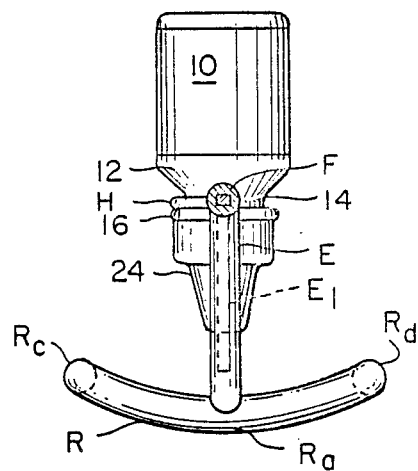
FIG. 6 is an end view of the same.

FIGS. 5 and 6 illustrate a hook ring embodiment. This embodiment has the same oval rim R as the previously described instrument. Vertical post E at the medial surface of rim $R_a$ extends up to support the horizontal post F from which extends a short rigid arm and hook ring H. The latter is positioned horizontally and equidistant from rim $R_c$ and rim $R_d$, and eccentrically toward the medial to permit the bottle 10 and nozzle tip 20 to be correctly positioned. Cross grooves G on rim $R_b$ are also present on this attachment to act as indicia for orientation purposes.

All posts (E, F or $E_2$) are easily made to be extendable when a friction grip is formed if the surface of the post is a tube (female), as in E and F, and the inner part is a shaft (male), as in $E_1$ and $F_1$; or, with the use of oblique spiral threading. If properly shaped, rotation of the tube and shaft is precluded.

Figure 7:
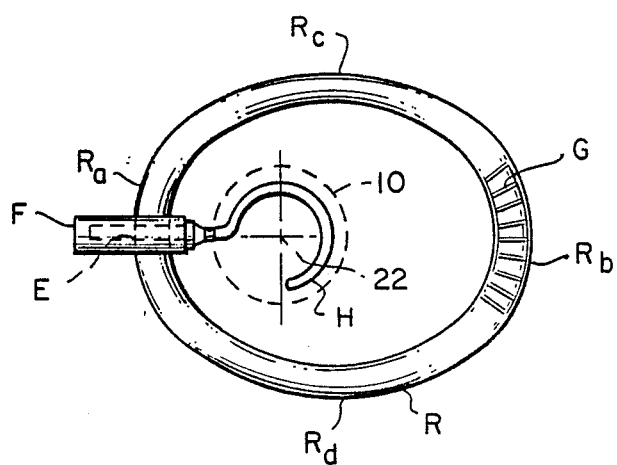
FIG. 7 is a plan view thereof.

FIG. 7 is a plan view of this hook ring embodiment.

To attach the hook ring instrument to a dispenser bottle, the hook ring H and its horizontal post F are securely grasped, the bottle 10 inverted and its neck 14 pressed into hook ring H. With bottle firmly attached, the instrument is ready for use as described in connection with FIG. 4.

Figure 8:
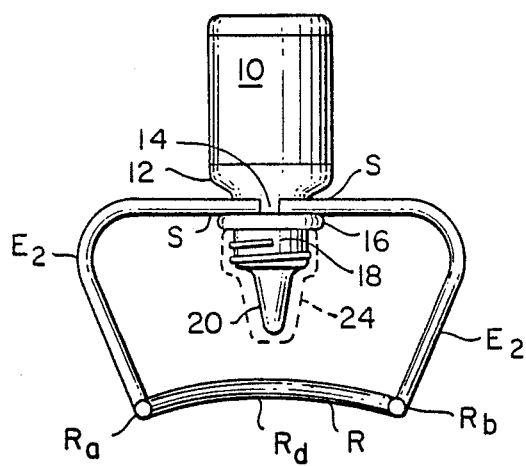
FIG. 8 is a front view of still another embodiment of the invention.
Figure 9:
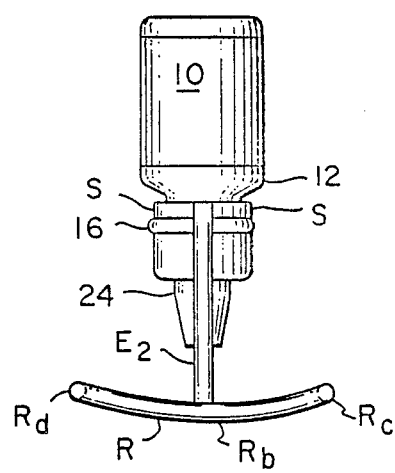
FIG. 9 is an end view of the same.

FIGS. 8 and 9 illustrate a further embodiment with a small rim R which fits within the orbital area. The design and appearance of the posts are similar to that of the posts in FIGS. 1 and 2 except that here, posts $E_2$ are placed on rim R at $R_a$ and $R_b$. The split ring S is aligned within the center area of rim R to bring the dispenser bottle 10 and nozzle 20 into the center of the rim and high enough over the eye are to avoid contact. Placement of the bottle into the instrument is as described for the embodiment of FIG. 2.

Figure 10:
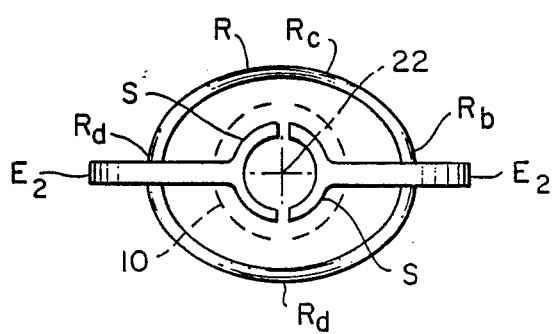
FIG. 10 is a plan view thereof.

FIG. 10 is a plan view detailing position of posts $E_2$ and split ring S inside of rim R.

Figure 11:
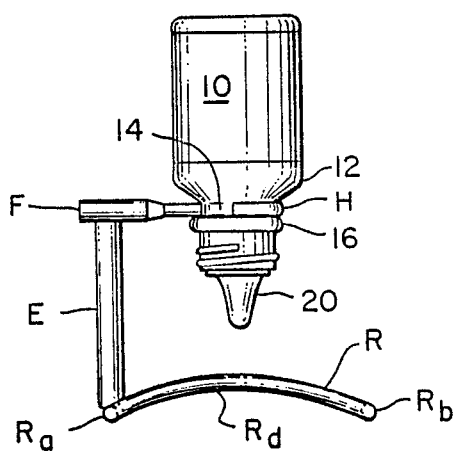
FIG. 11 is a front view of a fourth embodiment of the invention.
Figure 12:
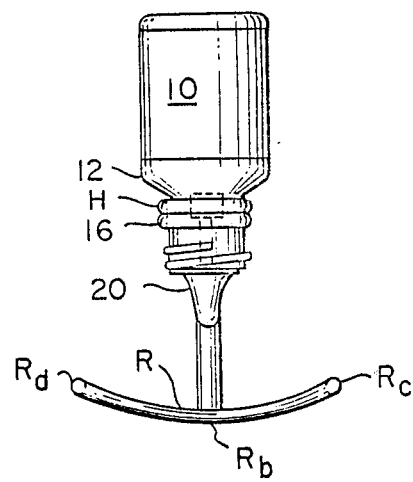
FIG. 12 is an end view of the same.

FIGS. 11 and 12 are front and end views of still another embodiment which consists of a small rim R and a vertical post E which is attached at $R_a$. The horizontal post F has an extension of a hook ring H which is located in the center of the rim. The attachment of this instrument is as described for the embodiment of FIG. 7.

Figure 13:
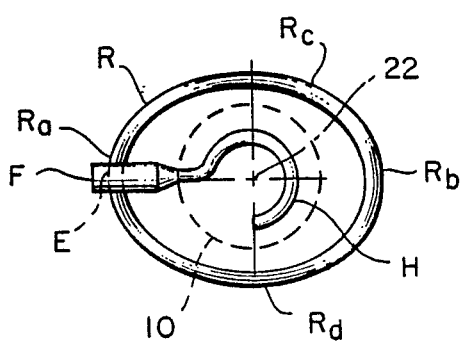
FIG. 13 is a plan view thereof.

FIG. 13 is a plan view of the parts relatively positioned.

Figure 14:
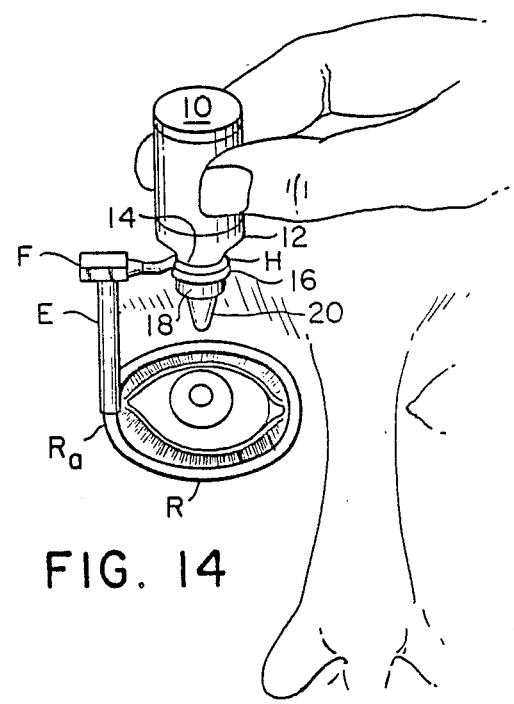
FIG. 14 is a perspective view showing this embodiment in use.

FIG. 14 is a perspective view of a hook ring H instrument positioned for use. Cap 24 is first removed. With the patient's head tilted back as far as possible or the patient in a prone position, the body of bottle 10 is grasped with thumb and forefinger. With vertical post E toward the lateral surface of the eye and with the eye open, the lower portion of the rim is positioned for contact just below the lashes of the lower eyelid. The eyelid is gently depressed with the rim to form a cul-de-sac or pouch. Rim R is now gently resting o lower orbital ridge. The instrument is seated and stabilized by rotating the lower rim which permits the upper rim to gently touch the open upper lid. Blinking reflexes may thus be controlled. The bottle is squeezed to expel solution onto eye. The same technique is used on both eyes.

Figure 15:
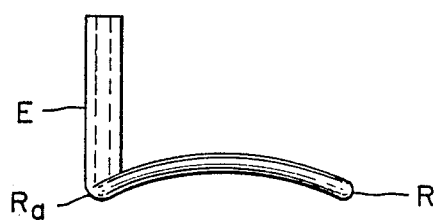
Figure 15:
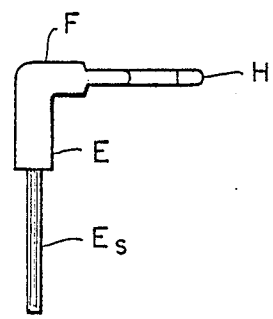
Figure 15:
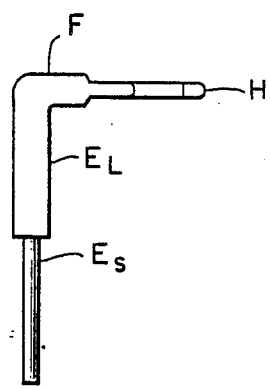
Figure 16:
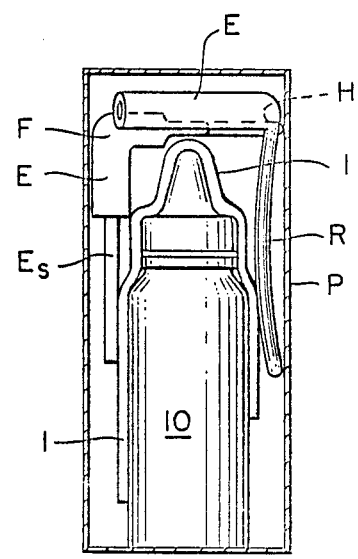
FIG. 16 is a side view of a package containing an instrument of the invention in disassembled state.
Figure 17:
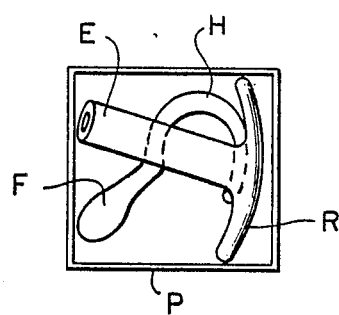
FIG. 17 is a top view thereof.

FIGS. 15 to 17 are similar to FIGS. 11 to 13, and illustrate a two piece, small rim device with hook ring for inserting into a package with a bottle of solution to be assembled later for use, without, in many instances, changing size of package. To assemble the instrument, the male shank $E_s$ of E is positioned into the female portion of E by frictional grip. To prevent rotation of rim R, several designs could be used:

(1) Multi-sided configuration to male shank $E_s$ with corresponding inner surface of female tube E,
(2) An ovoid male shank $E_s$ fitted into ovoid female of tube E, or
(3) A round male shank $E_s$ to round tube E, which requires a locking key and notch at the shoulders where both sections of E contact when assembled.

The attachment portion of the device shown in FIG. 15A has a short upper post E for use with the base rim portion of FIG. 15. The attachment portion shown in FIG. 15B has a relatively longer upper post $E_L$, e.g. suitable for use with a dispenser bottle having an unusually long nozzle core. When assembled the instrument resembles that of FIG. 11. In FIGS. 16 and 17, an instrument of the invention, including, e.g., a bottle 10 and insert I and the attachment portion of the device seen in FIG. 15, is shown in disassembled state in package P. Use of this device is as discussed and illustrated in FIG. 14.

There are several means by which the general use (small rim) hook ring attachment and the post surgical device (large rim) may be modified for compactness for purposes of packaging and carrying without removing the device from bottle neck, as will be discussed below.

It will be seen that each form of the invention comprises an instrument which is easily attached to a plastic eye dropper bottle to increase accuracy and safety while dispensing ophthalmic solution in post-surgical and general use.

For use in general care, the embodiment of this invention with a smaller oval rim is applied directly to the eyelids. After similar attachment methods are followed, this device assists in deflecting the lower lid and minimizes involuntary blinking.

The devices of the invention are of simple mechanical design, compact for easy packaging and storage, and safe and easy to use. Additionally, they are inexpensive to produce from standard plastic materials such as polyethylene, polypropylene, metal, or a combination of both plastic and metal.

Disposable and Compact Version

According to another aspect, the invention consists of an eye dropper bottle and positioning device combination, in which bottles are modified, e.g. for use with positioning means of special construction corresponding to that of the modified bottles or by integral incorporation of all or a portion only of the positioning means of the invention into the bottle manufacture. This would permit a more compact device for easy packaging, storing, and safe use at all times. Typically the present bottle design may be modified at the shoulder 12 and upper part of body 10 to permit securing a positioning device of the invention, consisting of a rim R and generally one vertical (or main) post E and one horizontal (or stub) post F. In some instances, two main and stub posts may be provided.

In another embodiment to be completely disposable, the bottle is modified to include the positioning means as an integral part of or partially attached near the shoulder 12 at upper part of an otherwise convention plastic squeeze-type bottle 10 used for dispensing drops of liquid eye medication or solution.

It is most desirable to discard the bottle 10 with the positioning device of the invention after contents have been completely used, or after there is no longer any need for the remaining solution.

It is most desirable to discard the bottle 10 with the positioning device of the invention after contents have been completely used, or after there is no longer any need for the remaining solution.

Except where otherwise indicated, we refer to a single post instrument. The two post instruments can also be employed where desired, but confines approach to the bottle cap 24 and may be more involved in the manufacturing process.

According to the invention, solution dispenser bottles are modified at shoulder for disposable instruments with features for compact use by:

I. Internal attaching means:

A rigid hollow straight plastic type tube T is formed horizontally within the bottle at the shoulder region with openings or orifices (round or rectangular) at opposite surfaces. Alternatively, a recessed, rigid (round or rectangular) box-like opening is formed at the shoulder on one or two surfaces.

Retentive means includes any of the following:

(1) A friction grip round surface 30 (FIG. 18) with key lock(s) $K_L$ secures post F into tube T and obtains correct position of post E and rim R for use, storage or carrying. The short round horizontal post F is withdrawn slightly to disengage key locks $K_L$, vertical post E is rotated to desired position and post F is pushed to re-engage key locks. In a "use" position, post E and rim R are up; to store the assembly in its package, post E is down and rim R is under the bottle base 11, e.g., see FIG. 35.

(2) A screw in spiral threaded tip 32 (FIG. 19) of post F is received into matching inner spiral 34 of tube T to place rim R into use position. A reverse ½ turn lowers rim R under the bottle to store or carry in its package.

(3) A snap on round friction grip 36 (FIG. 20) of post F is received by the key lock(s) $K_L$ and grooves 38. The device is rotated to desired position for use, or to store and carry, rim R is under the bottle base.

Figure 21:
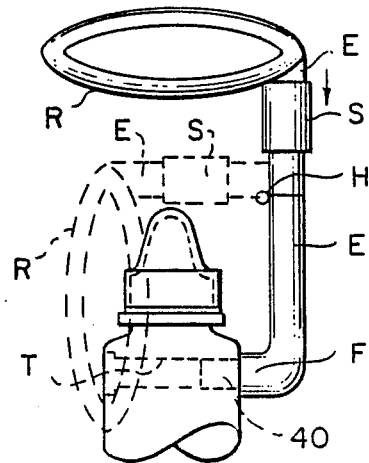

(4) Rectangular or square friction means 40 (FIG. 21) provide for retention of post F within the orifice of tube T to support the split vertical post E with hinge H (metal or plastic), and a threaded or friction slide sleeve S (also metal or plastic) to provide rigidity to post E when extended to vertical position for use. A hinge may also be positioned on the medial surface as well as at split area of post E. To insert the assembly into a package for carrying, the sleeves may be slid or screwed toward or away from rim R (arrow) and allow the device to be folded (indicated by dashed lines), leaving post F in place at the shoulder.

Figure 22:
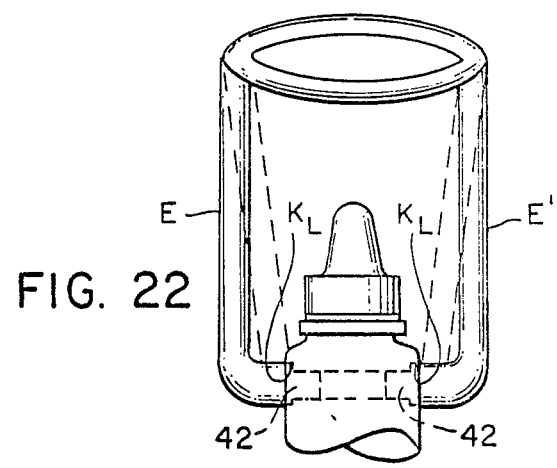

(5) Two reciprocal posts E, E' (FIG. 22) have snap in or round friction retentive protrusions 42 on horizontal posts F to engage with key lock $K_L$ at one orifice. Key lock $K_L$ is disengaged to rotate posts E and rim R for use or to position rim R below bottle base to store or carry.

Figure 23:
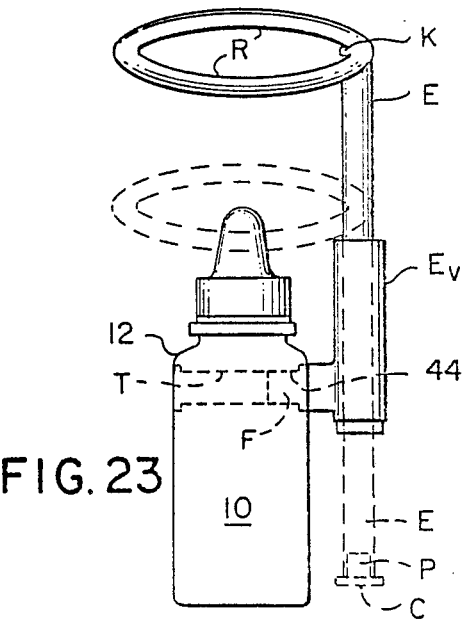

(6) Square or rectangular friction means 44 (FIG. 23) are provided for retention of post F within an orifice of tube T, to support vertical-adjustable friction post E within a vertical tube $E_v$ to prevent rotation of post E and rim R. (Both post and tube are preferably ovoid in cross section.) Friction post E slides up for use and down for storage or carrying. A small knob K on median surface of post E near rim R, and plug P with lip, or cap C applied at the opposite end of post E, after assembly, function as guide stops for regular or long cone.

(7) A telescopic vertical post E (described below) may also be employed.

Figure 24:
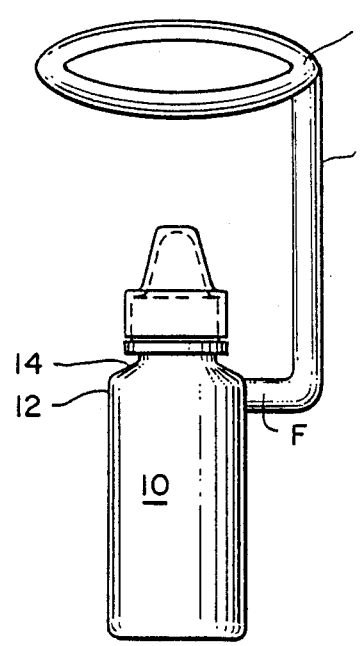
FIGS. 24 through 26 are somewhat diagrammatic front views of alternate embodiments of an instrument according to the invention in which the bottle and device or a portion of the device are integrally formed.
Figure 24A:
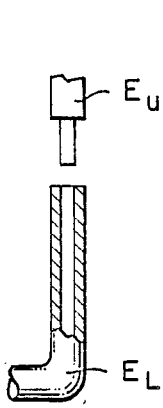

II. External Attaching Means (from the shoulder region of the bottle):

FIG. 24 illustrates an instrument consisting of an integral bottle-and-device, the device consisting of a main post E supported by stub post F at the shoulder, with rim R at the opposite (first) end. The assembly is totally disposable. Referring to FIG. 24A, a partial post $E_L$ may be formed integrally with the bottle, with an orifice (or post) for attachment of the upper part $E_u$ of the post supporting rim R.

Figure 25:
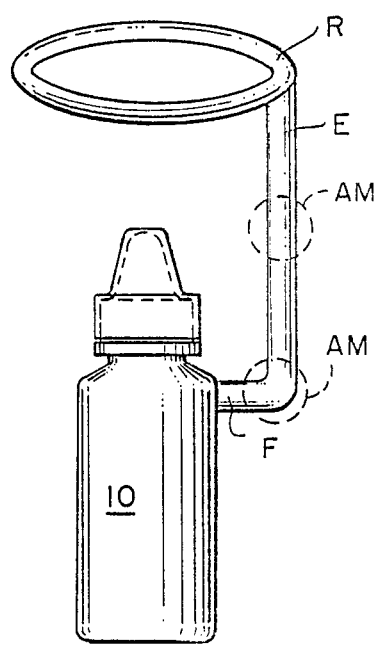

Referring now to FIG. 25, by modifying the attaching means area where post F and post E intersect, any of the various types of internal attaching means (AM, described above) could be utilized. Various types of vertical posts E could likewise be used.

Figure 26:
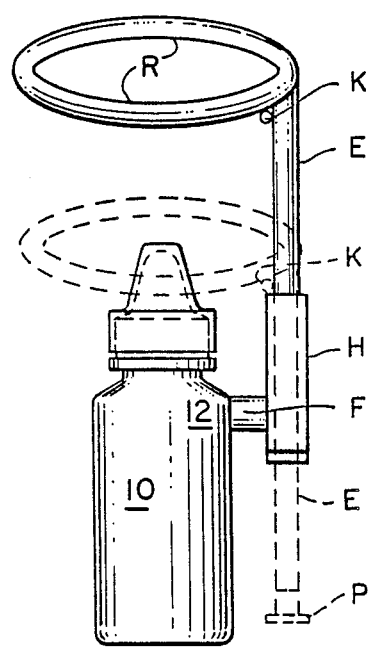

FIG. 26 shows a short rigid horizontal extension of post F extending from shoulder region 12 to support a vertical ovoid hollow tube H into which there is placed with friction fit vertical ovoid post E, thus permitting extended and retracted positioning of rim R.

III. Surface Attaching Means (non projecting):

Dispensing bottles could be made with various retention means at shoulder region 12 and upper part of the bottle body 10 to include:

(1) oblique spirals;
(2) friction grip locking devices;
(3) full or interrupted horizontal grooves; or
(4) full or interrupted horizontal spirals. These would provide excellent retention for the primary apron A (FIGS. 27A-D) supporting the partial or full device. Apron A could be screwed on, locked into position, or snapped into place.

Figure 27A:
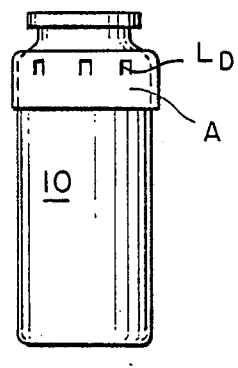
FIGS. 27A through 27D are similar views of still another embodiment of the invention including an apron for attachment for the positioning device upon the bottle.
Figure 27B:
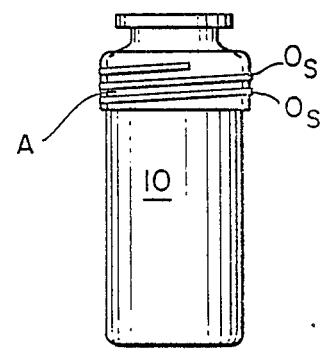
Figure 27D:
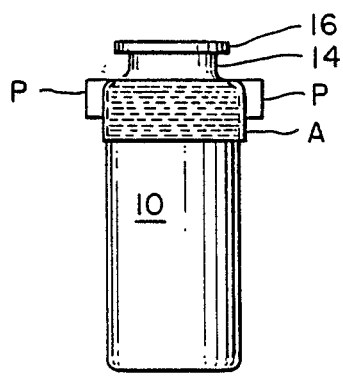
Figure 27C:
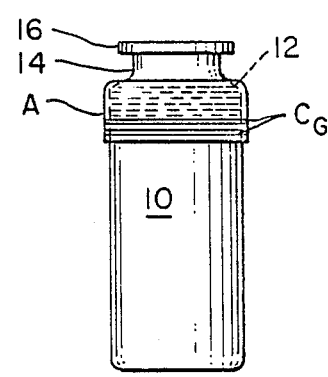
Figure 29:
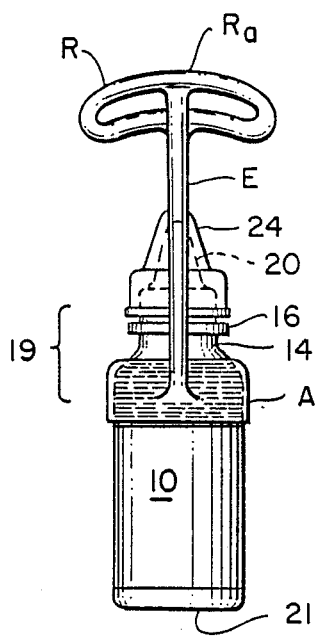
FIG. 29 is a side view of same.
Figure 28:
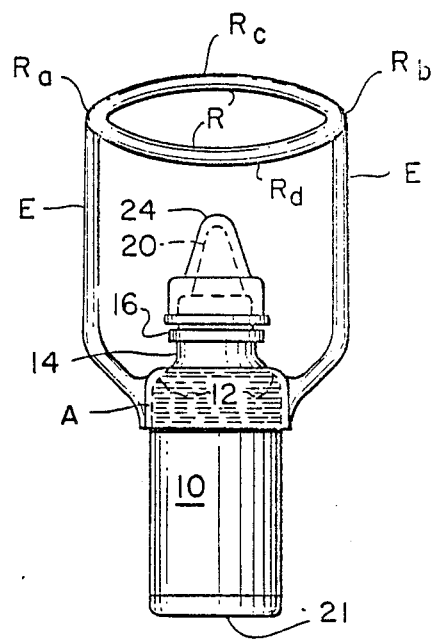
FIG. 28 is a front view of still another preferred embodiment.
Figure 31:
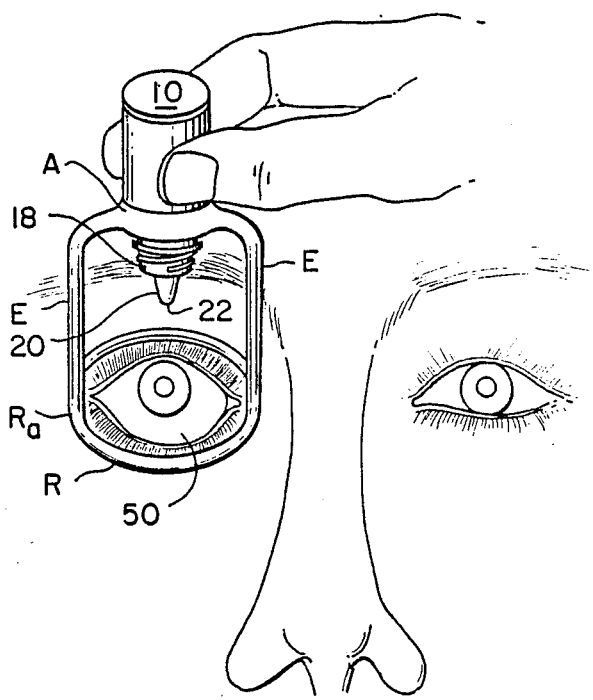
FIG. 31 is a perspective view showing this embodiment in use.
Figure 30:
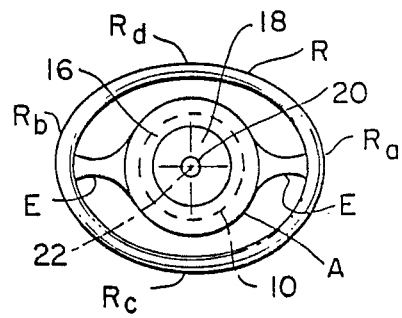
FIG. 30 is a plan view thereof.

The illustrations in FIGS. 27A-C, although on outer surface of apron A, would be applicable to the above described surface retention means.

Since there are no projections beyond the regular bottle surface, there would not be any interference with the manufacturer's production process. The attachment and positioning device is disposable, and cannot be employed with regular or unmodified dispenser bottles.

According to still another aspect of the invention, in order to eliminate the necessity of making changes to the bottle, there is applied a rigid or semi-rigid plastic full circular or an open apron A, with retention means for affixing the apron permanently to the bottle shoulder region 12 and upper portion of the bottle body 10, e.g. by use of rapid setting epoxy adhesive, before inserting the bottle with solution into a package. Other retentive means for apron A could include:

(1) a slight, narrow circular elevation near lower inner edge;

(2) beading at lower margin or on inner surface; or (3) vertical ribs, rough or pebbly surface. The apron A may incorporate one of the attaching means described above, or may be employed with a secondary apron A', the secondary apron carrying the attachment means and adapted for fixed engagement upon the apron A attached to the bottle.

FIGS. 27A–D illustrate front views of several aprons A. The outer surface of primary apron A has positive defined means to assist in obtaining a secure position for secondary apron A', such as:

(a) Assorted friction grips with locking devices $L_D$ (FIG. 27A);

(b) screw on with well-defined oblique spirals $O_S$ (FIG. 27B);

(c) snap on with circular groove(s) $C_G$ near lower edge (FIG. 27C); or (d) squared edge on upper outer shoulder with some projections P (square or rectangular) to enhance seating and locking with friction grip into inner corresponding means of apron A' (FIG. 27D).

Figure 32:
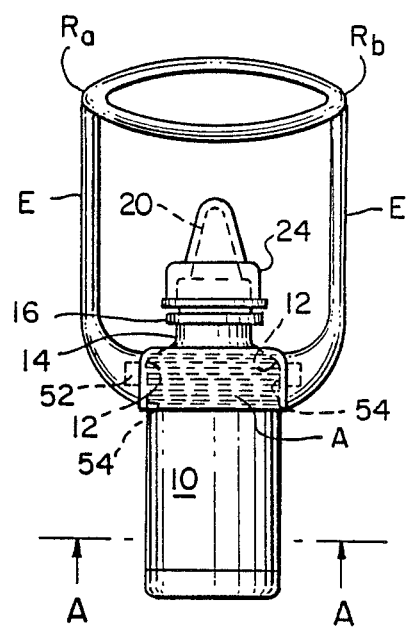
FIG. 32 is a front view of another embodiment.
Figure 33:
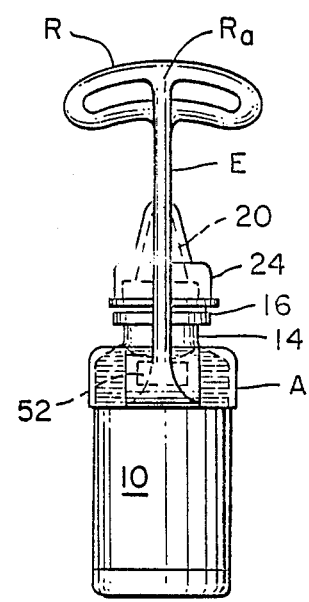
FIG. 33 is a side view of same.
Figure 34:
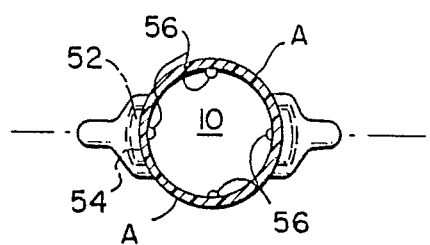
FIG. 34 is plan section at A—A of FIG. 32.

The outer surface of secondary apron A' has means to support the vertical post(s) E and rim R, either by an attached or movable horizontal post(s) F supporting a one piece rigid attachment, or attaching means resembling, e.g. FIGS. 18–23 and 28–31, or a two-piece attachment with features from, e.g. FIGS. 32–34; or means for having a more compact device which will permit rotation of post F, hinge, or vertical movement of post E and rim R, e.g. as in FIGS. 18–23 and 35–41.

The embodiments of FIGS. 28 to 41, to be truly disposable, should be an integral part of or partially attached at the shoulder region 12 at upper part of conventional plastic squeeze-type bottle 10 used for dispensing drops of liquid eye medication or solution.

Again, it is most desirable to discard the bottle 10 with the device after contents have been completely used or there is not longer any need for the remaining solution.

The preferred embodiment shown in FIGS. 28–31 consists of a small oval rim R which is contoured to fit within the orbital area, with the rim R at $R_c$ and $R_d$ concave at the bottom. Two vertical posts E are attached to rim R at $R_a$ and $R_b$ and the opposite ends converge inwardly to attach to the full circular apron A over the shoulder 12 of the bottle 10. A device with only one vertical post attached to rim R at $R_a$ and to one side of apron A would be an excellent attachment. The apron is constructed of a thin, rigid plastic which rests on the shoulder 12 and upper part of bottle 10. This apron A has a secure fit which could be enhanced by some fine beading on inner surface near bottom edge, and/or a knurled or rough inner surface or the apron could be provided with internal screw threads to engage external threads provided on the bottle (not shown).

The attachment is seated by passing the cap 24 and nozzle 20 through the orifice of apron A and, while firmly holding the apron, pressing, and with a back and forth rotating motion gradually bring the apron to a positive and secure position. The rigid attachment supports the bottle 10 in a vertical position and also places the nozzle tip 20 within the central are of the rim R. The nozzle tip 20 is high enough above the rim R to prevent contact with the eyelids or eyelashes when applied to the eye for use.

By applying rapid setting epoxy adhesive to shoulder, upper part of bottle and inner surface of apron A, this attachment could be permanently secured onto the bottle by the manufacturer, thus creating a completely disposable instrument.

If the attachment is placed within the package with the bottle of ophthalmic solution, the patient could be encouraged to apply epoxy adhesive or other glue or assemble and use without adhesive.

The remaining bottle parts are: nozzle aperture 22, nozzle spiral 18, neck-and-shoulder region 19, base of the neck 16, and base of bottle 21.

In use, cap 24 is carefully removed. With the individual's head tilted back as far as possible, or even better, by assuming a prone position with head tilted back, the body of bottle 10 is grasped with thumb and forefinger. With the vertical posts E toward the medial and lateral surface of eye and with the eye open, lower portion of rim R is gently positioned for contact with lower eyelid just below the eyelash. The eyelid is then depressed with the rim to form a cul-de-sac 50. The lower margin of rim R is now resting near the edge of inferior orbital ridge area. Seating of the instrument is completed by rotating the lower rim to permit the upper rim to gently rest on the outer surface of open upper eyelid, thereby stabilizing the whole unit.

Blinking reflexes may thus be controlled long enough to squeeze the bottle to expel the required amount of solution onto the eye in area of the cul-de-sac. The procedure is repeated for other eye. Cap 24 is replaced carefully to cone 20 to avoid inducing contamination to cone. It is easier if the right hand is used when servicing the right eye and conversely for the left.

Referring now to FIGS. 32 and 33, a disposable embodiment of the invention is created in two parts. The apron A is made with a projecting rectangular key 52, slightly curved to conform to the curvature of the bottle at shoulder 12 and body 10, as an integral part with a minimum of 3/32 inch width in order to provide adequate surface area engagement.

The apron A is made separately with the projecting rectangular key on opposite surfaces (shown dotted). The support posts E have built-in inward tension, with recesses 54 matching the rectangular keys of apron A, to provide supportive connection. Substituting projecting round keys on the outer surface of apron A with somewhat similar dimensions and support posts E with recess matching round keys and on key lock (not shown) will enable rotation of vertical posts E and rim R for use and for storage or carrying, and have compact features.

Referring to FIG. 34, the lower inside surface of the apron provides at least four small projections 56 to enhance gripping action.

The apron A is placed on the bottle and attached, e.g. with epoxy adhesive, by the manufacturer to produce a totally disposable unit. The remaining portions of the positioning device are placed in position by the patient, by extending the posts to permit the post keys to securely engage the projections on the apron.

Use of the unit is as described for previous embodiments.

Figure 18:
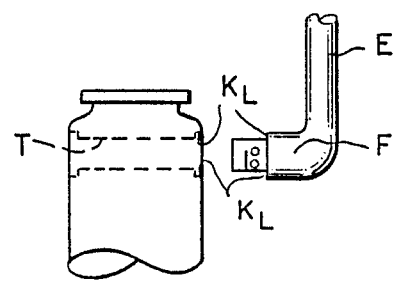
FIGS. 18 through 23 are somewhat diagrammatic front views of alternative embodiments of an instrument according to the invention in which the dispenser bottle is modified for attachment of the positioning device.
Figure 35:
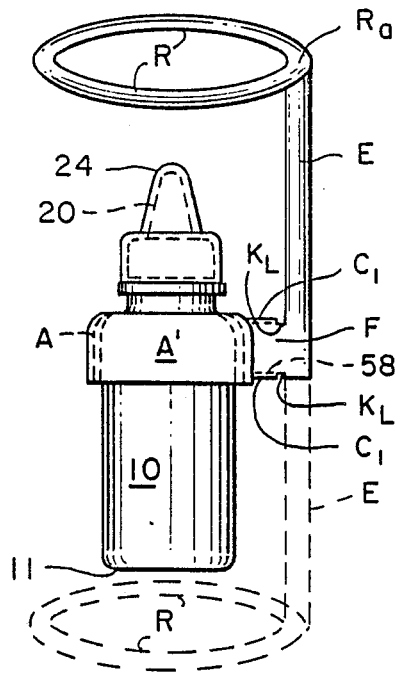
FIGS. 35 and 36 are front and side views of still another embodiment of the instrument of the invention.
Figure 36:
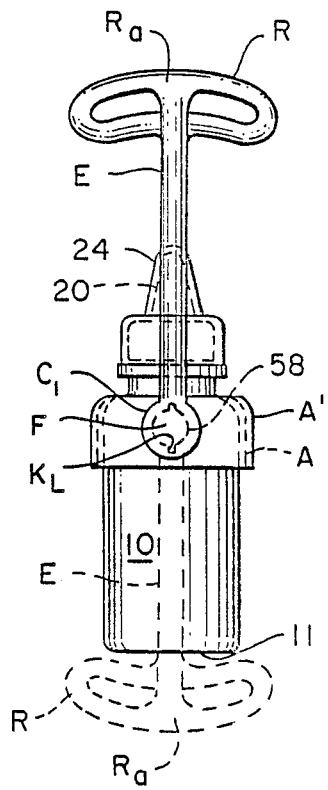

FIGS. 35 and 36 show front and side views of a disposable and compact embodiment of the invention utilizing retentive means consisting of the friction grip round surface 58 of post F (e.g., as illustrated in FIG. 18) adapted to apron A', disposed over apron A. This device has a horizontal round plastic cylinder $C_1$, with two key locks $K_L$ at the edge of the rim of cylinder $C_1$ on opposite sides in a vertical position. The horizontal post F fits securely with tight friction into cylinder $C_1$. Matching key locks $K_L$ are located on surfaces where post F joins post E and in line with vertical position of post E. When the key locks are in apposition, they permit vertical post E, which supports, at $R_a$, a small rim R, to be locked into proper and secure position for use or storage. The short round horizontal post F is withdrawn slightly to disengage key locks $K_L$; post F is rotated to bring post E and rim R to the desired position and pushed in to reengage the key locks. The use of this small rim device is the same as described above. The "store" position (indicated in dashed line) brings rim R below the bottle base 11, and permits replacing the bottle with device intact into original package. This device could also be attached to apron A.

Figure 19:
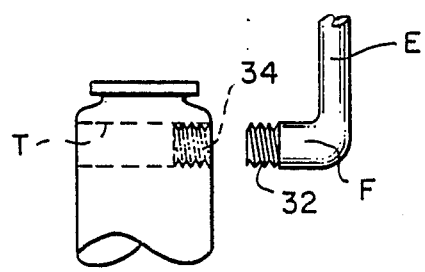
Figure 20:
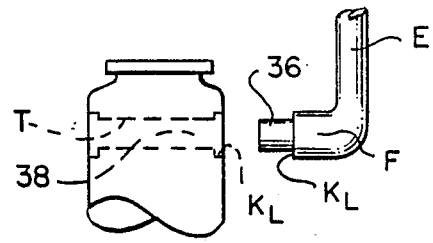

Other retentive means discussed in FIGS. 19-20 could very easily be affixed to apron A' or apron A. The screw-in spiral threaded tip of post F into matching receptacle on apron (FIG. 19) or the snap-on round friction grip of post F to the apron (FIG. 20) provides easy means to position post E and rim R for use or under the bottle to store or carry. These compact devices remain on bottle when replaced into package.

Figure 37:
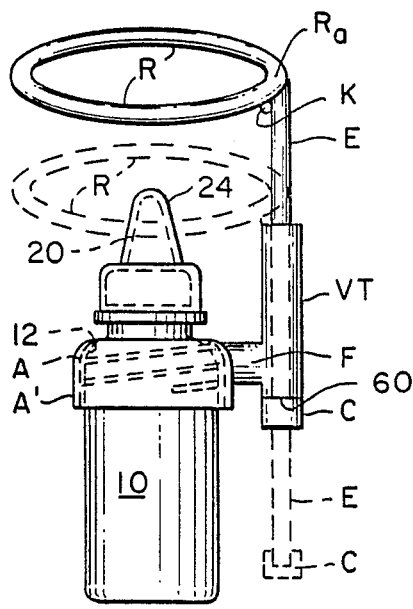
FIG. 37 is a front view of yet another embodiment.

FIG. 37 shows another embodiment, referred to as vertical adjustable friction post, the device having two sections. Apron A' is made with attaching means on inner surface to assist in being secured to apron A, which is already permanently attached to bottle 10 at the shoulder 12. A short horizontal post F at the side of apron A' supports a vertical tube $V_T$. The inner surface of tube $V_T$ is ovoid, or rectangular, or of any means to prevent rotation of the vertical post E having a similar configuration, with a tight friction grip of tube $V_T$ to post E. Post E supports rim R at $R_a$. A small knob K located on inner surface of post E where it joins rim R serves as a stop when retracting post E.

To assemble, post E is pushed down and through tube $V_T$, starting at the top orifice. A tight fitting cap C is placed over the lower end of post E. The length of cap C is determined by nozzle 20 length and also acts as a stop when extending post E.

To use the device, post E is pushed up at cap C until the edge of cap C touches the lower edge 60 of tube $V_T$. Rim R is now at a proper and safe distance from nozzle 20 which is centered within the area of rim R. Cap 24 is removed from nozzle 20 and the process is continued as previously described for use of intraorbital (small rim) device. Cap 24 is replaced securely after use.

When not in use, the bottle is left in upright position with the device attached.

To store in a package, the device is held at tube $V_T$ and post E retracted with rim R by pushing down at $R_a$ over post E (to avoid breaking rim R) until knob K touches upper edge of tube $V_T$ (dashed line position). The rim R is now level with and surrounding bottle cap 24, and is ready to be replaced in the package without removing the device from the bottle.

Figure 38:
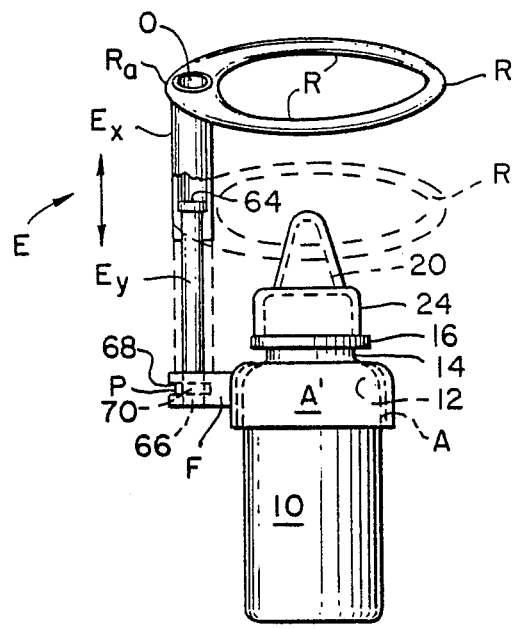
FIGS. 38 through 40 are front, side and top section views, respectively, of still another embodiment of the instrument of the invention.
Figure 39:
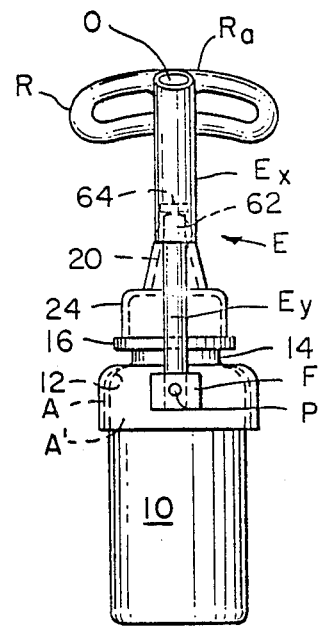
Figure 40:
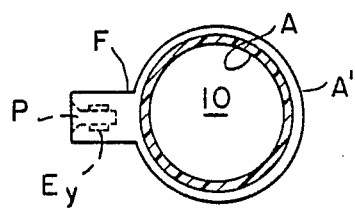

FIGS. 38 through 40 show a telescopic, retractable-extendable embodiment of the instrument, which has a vertical post E consisting of two sections. The upper section $E_x$ is a round tube which is attached to and supports the small oval ring R at $R_a$, forming a circular opening 0 at this point. The lower inner part of the tube has a squared shoulder 62 for about a height of one quarter inch from the end. The lower section $E_y$ of post E is approximately the same length as upper section, but has a square shape to securely grip the inner squared part of the upper tube. The upper tip of the lower post has a round flat rim 64 to securely fit the inner round surface of the tube, providing stability during movement and a stop on the extension. Near the lower end of the squared post there is a horizontal round hole 70 in line with the position of rim R.

The lower horizontal post F extending from the side of apron A' has a vertical squared hole 66 near the end and a horizontal round hole 68 extending through the mid area from tip to beyond the squared hole.

To assemble the device, the squared post $E_y$ is pushed through round hole O at $R_a$, through squared inner part of the tube having a tight friction grip, to emerge through the tube. While holding a finger over hole O and flat rim 64 at $R_a$, the bottom end of the squared post is securely placed into the squared hole 66 without protruding beyond the lower surface of post F. A round plastic or metal nail P with flat head is pushed thru aligned horizontal holes 68 and 70 to penetrate into post F securing post $E_y$.

Post Ex is extended to use the device and retracted (dashed line position) to bring the rim R over cap 24 for storage.

The method of use is the same as described for previous small rim devices.

Figure 41:
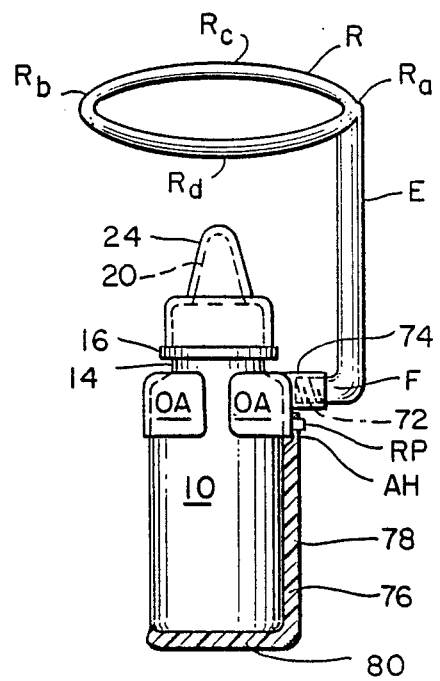
FIGS. 41 and 42 are somewhat diagrammatic front views of still other embodiments of the invention.

FIG. 41 shows another embodiment utilizing the open apron $O_A$, which is a circular apron with a vertical split, made of thin rigid plastic with sufficient flexibility to securely fit onto the shoulder 12 and upper part of body 10 of bottle. The retention means is a horizontal post F having oblique spirals 72 for the screw in spiral tip which is secured when rotated into the corresponding inner spiral of the small tube 74 on the side of open apron $O_A$. The lower end of the rigid post E is attached to post F and extends in a vertical position to attach to the small rigid ovoid rim R at $R_a$, supporting the rim R in a horizontal position. Nozzle 20 and cap 24 are centered in the mid area of rim R which is high enough above nozzle 20 to prevent any contact with eye lids or eye lashes when in use.

Should there be any concern about adequate and secure retention of any apron, a cradle 76 of rigid plastic can be used. This cradle will not be required if details are precisely executed and bottles are standard in size. To attach a cradle 76 to any apron, a rectangle or small round projection $R_P$ from apron $O_A$ under post F or on the opposite surface of post F permits the cradle arm 78 to be snapped into position after the cradle base 80 is placed under the bottle base. If desired, additional tension of cradle base 80 to bottle can be achieved by either a two piece friction cradle arm or a rotating vertical cradle arm. Two cradle arms can be also used, one on each opposite surface.

This embodiment can easily be changed from the use position to the store or carry position by rotating post F one half turn, bringing rim R under the bottom of the bottle. The cradle arm 78 or cradle base 80 will not interfere with any movement of post E or positioning of rim R.

Use of this device is the same as previously discussed.

Figure 42:
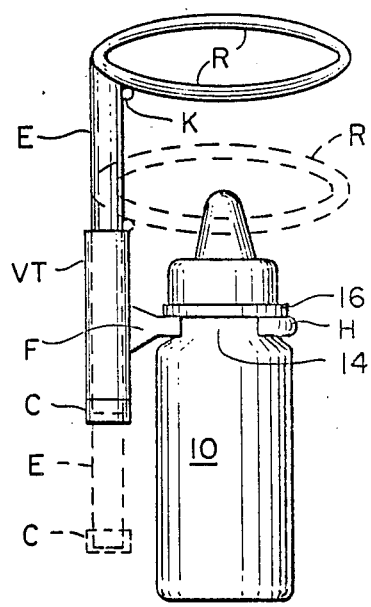

Other embodiments are within the following claims. For example, the embodiments of FIGS. 5 to 7 and FIGS. 11 to 14 can be modified to utilizing the ideas and suggestions brought forth earlier for retentive means having internal attaching means (FIGS. 18–23), and incorporating the various designs and illustrations discussed for making compact devices (FIGS. 28–41). In this way, many different models of compact devices can be made utilizing the single post hook ring (see, e.g., FIG. 42) with small rim for general use (or even the double post) and the larger rim for postsurgical use. All parts may be formed of rigid plastic, although metal or a combination of each could be used.

Any large rim R attachment which is used for postsurgical and general use could be converted to a disposable and compact type by utilizing the described invention.

All of the described embodiments could be attached to an apron and assembled by the manufacturer or by user.

Using rapid setting epoxy adhesives or the like, any apron-type eye drop dispenser attachment could be permanently attached to a bottle, thereby making it totally disposable.

Bottles can be molded with the post(s) emerging from the shoulder, providing several possibilities such as:

(1) one or two posts used to support the rim;
(2) a one-piece unit could be made;
(3) a two-piece attachment, having either one or two posts, utilizing sliding frictional grip male post(s), hinges or rotating post(s) and aprons to be assembled by the patient.

It will be seen that each form of the invention comprises an instrument produced as a complete or partial unit together with the plastic squeeze type eyedropper bottle as an integral part thereof, or may exist as a separate partial or complete unit to be easily attached to the bottle and thus become readily disposable when the solution has been fully used or is no longer required.

Other features and benefits of the disposable version of this invention are as follows:

(a) avoids necessity in many instances for the patient to secure the attachment to the bottle, but if necessary, attaching the instrument could be easily accomplished by user;
(b) will not interfere with holding bottle during administration of drops;
(c) permits ease and safety for direct application to eyelids, retracts lower eyelid to form a cul-de-sac, and minimizes blinking reflexes;
(d) directs bottle nozzle tip to proper height and position over the eye to prevent accidental contact with eye;
(e) prevents nozzle tip from contacting sources of contamination;
(f) prevents prolonged use and decreases the opportunity for other persons to use same dispenser attachment, thereby preventing possible spread of infection;
(g) avoids waste of solution by directing deposit of solution to correct spot;
(h) permits ease and safety in use of a bottle in the orbital area by leaving surgically involved areas of the eye undisturbed;
(i) provides stability by assisting the elderly or incapacitated in effective application of solutions;
(j) permits young individuals to self-administer drops;
(k) restores self-confidence and independence to patients by the ability to administer their own drops.
(l) should prevent patients from using wrong bottle of solution, thereby avoiding accidents.

These devices of the invention are of simple mechanical design, compact for easy packaging and storage, safe and easy to use. Additionally, they are inexpensive to produce from standard plastic materials such as polyethylene and polypropylene and in the future could be made from biodegradable materials. Other equivalent means of attachment to the bottle will occur to the worker skilled in the art. For example, the part(s) could snap into a socket or sockets on the bottle; the post could extend upwardly from a holder fitting around and/or under the bottle and separately affixed to it; such as a cradle device etc.

Many changes in details of the above-described embodiments are easily introduced without altering the benefits of this invention which will provide individuals with an easy, safe and sanitary means to maintaining general and post-surgical eye care. It is therefore intended that the scope of the invention be limited only by the proper interpretation of the appended claims.

I claim:

1. An instrument for delivery of drops of liquid eye drop solution into the eye of a patient for post-surgical and general treatment, said instrument comprising:

a squeeze-type dispenser bottle comprising a body defining a volume for eye drop solution, said body having a neck and shoulder region and a base, and having a nozzle disposed above said neck and shoulder region and defining an orifice for delivery of solution from said volume, and a device for positioning said nozzle relative to an eye of a patient to be treated, said device comprising
a generally oval ring contoured to fit the intraorbital or periorbital area of a patient's body,
at least one post extending from said oval ring generally perpendicular to a plane of said oval ring, said post comprising a main section having a first end joined to said oval ring and a second end, and a stub post element disposed to extend between said second end and an apron member, said stub post element extending generally perpendicular to the axis of said main post section, and means for attachment of said post in the region of said shoulder and upper part of the body of said bottle comprising
said apron member sized and constructed for fixed engagement upon said body, encircling said nozzle, and comprising a first apron portion adapted to engage upon said bottle generally in said shoulder region and defining an opening for passage over said nozzle and said neck, and said apron member further comprising a second apron portion depending from said first apron portion to extend about the body of the bottle in a region more remote from said neck.

2. The instrument of claim 1 wherein said means for attachment is adapted for selective disposal of said oval ring in a first (use) position, with said ring centered about and spaced from said nozzle, and a second (store and carry) position with said oval ring disposed more adjacent the body of said bottle.

3. The instrument of claim 2 wherein said stub post is adapted for rotation in said orifice, and said oval ring in said second position is disposed adjacent said bottle base.

4. The instrument of claim 2 or 3 wherein said apron further comprises a sleeve sized and constructed for rotational engagement about said stub arm.

5. The instrument of claim 1 wherein said main post section comprises a post element and a tube element, said post element being sized for frictional sliding engagement within said tube element.

6. The instrument of claim 1 wherein said main post section comprises a hinge element.

7. The instrument of claim 1 wherein said stub post element is an integral element of said apron.

8. The instrument of claim 1 wherein said device comprises at least two posts, the stub arm of each post defining an orifice, and
    said apron further comprises two projecting key elements sized and constructed for engagement within said stub post orifices.

9. The instrument of claim 1 wherein said stub post element is fixedly joined to said main post section at said second end, and said stub post element is sized and adapted for fixed engagement within an orifice defined upon said bottle for positioning of said oval ring of said device relative to said bottle.

* * * * *

UNITED STATES PATENT AND TRADEMARK OFFICE
CERTIFICATE OF CORRECTION

PATENT NO. : 4,960,407

DATED : October 2, 1990

INVENTOR(S) : Samuel M. Cope

It is certified that error appears in the above-identified patent and that said Letters Patent is hereby corrected as shown below:

Col. 3, line 17, change "ma" to --may--.

Col. 6, line 14, change "resting o" to --resting on--.

Col. 7, lines 28-31, delete entirely, they are redundant to lines 24-27.

Col. 8, line 56, insert a line between "spirals." and "These".

Col. 9, line 13, insert a line between "surface" and "The".

Col. 10, line 7, change "are" to --area--.

Signed and Sealed this

Tenth Day of March, 1992

Attest:

HARRY F. MANBECK, JR.

Attesting Officer

Commissioner of Patents and Trademarks